(12) United States Patent
Jacobs et al.

(10) Patent No.: US 6,489,363 B2
(45) Date of Patent: Dec. 3, 2002

(54) PHARMACEUTICAL SOLUTIONS OF MODAFINIL COMPOUNDS

(75) Inventors: Martin J. Jacobs, West Chester, PA (US); Bradley T. McIntyre, Thorndale, PA (US); Piyush R. Patel, Wallingford, PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 09/974,473

(22) Filed: Oct. 10, 2001

(65) Prior Publication Data

US 2002/0099097 A1 Jul. 25, 2002

Related U.S. Application Data

(60) Provisional application No. 60/239,488, filed on Oct. 11, 2000.

(51) Int. Cl.⁷ .............................................. A61K 31/16
(52) U.S. Cl. ....................................... 514/615; 424/455
(58) Field of Search ........................... 514/618; 424/455

(56) References Cited

U.S. PATENT DOCUMENTS

| 4,177,290 A | 12/1979 | Lafon |
| 4,927,855 A | 5/1990 | Lafon |
| 5,180,745 A | 1/1993 | Lafon |
| 5,618,845 A | 4/1997 | Grebow et al. |
| 6,200,968 B1 | 3/2001 | Dickason et al. |
| RE37,516 E | 1/2002 | Grebow et al. |

FOREIGN PATENT DOCUMENTS

| WO | WO 99/25329 | 5/1999 |
| WO | WO 01/58439 | 8/2001 |

OTHER PUBLICATIONS

Rambert, F.A. et al., *Neuropschychopharmacology*, 1994, 10(3S), 169S.

*Primary Examiner*—James H. Reamer
(74) *Attorney, Agent, or Firm*—Robert T. Hrubiec; Eric K. Voelk

(57) ABSTRACT

Pharmaceutical compositions of modafinil compounds, and pharmaceutical, non-aqueous compositions of modafinil compounds in organic solvents are disclosed, along with their use in the treatment of diseases.

39 Claims, No Drawings

PHARMACEUTICAL SOLUTIONS OF MODAFINIL COMPOUNDS

This application claims the benefit of Provisional application Ser. No. 60/239,488, filed Oct. 11, 2000.

FIELD OF THE INVENTION

The invention relates to pharmaceutical compositions comprising a modafinil compound in solution, and in particular, to non-aqueous solutions comprising at least one organic solvent. The invention is further directed to methods of using of the compositions in the treatment of diseases.

BACKGROUND OF THE INVENTION

Modafinil ($C_{15}H_{15}NO_2S$), is 2-(benzhydryl-sulfinyl) acetamide, and is also known as 2-[(diphenylmethyl) sulfinyl] acetamide.

Modafinil has been described as presenting a "neuropsychopharmacological spectrum characterized by the presence of excitation with hyperactivity and of hypermotility; and by the absence of stereotypy (except in high doses) and of potentialization of the effects of apomorphine and amphetamine" (U.S. Pat. No. 4,177,290; hereinafter the "'290 patent," which is incorporated in its entirety herein by reference). A single administration of modafinil results in increased locomotor activity in mice and increased nocturnal activity in monkeys (Duteil et al., Eur. J. Pharmacol. 180:49 (1990)). Modafinil has been successfully tested in humans for treatment of idiopathic hypersomnia and narcolepsy (Bastuji et al., Prog. Neuro-Psych. Biol. Psych. 12:695 (1988)).

Other uses of modafinil have been presented. U.S. Pat. No. 5,180,745, incorporated in its entirety herein by reference, discloses the use of modafinil for providing a neuroprotective effect in humans, and in particular for the treatment of Parkinson's disease. The levorotatory form of modafinil, i.e.,(-)benzhydrylsulfinyl-acetamide, may have potential benefit for treatment of depression, hypersomnia and Alzheimer's disease (U.S. Pat. No. 4,927,855, incorporated in its entirety herein by reference). European Published Application 547952 (published Jun. 23, 1993) discloses the use of modafinil as an anti-ischemic agent. European Published Application 594507 (published Apr. 27, 1994) discloses the use of modafinil to treat urinary incontinence.

Preparations of modafinil having a defined solid particle size have been described in U.S. Pat. No. 5,618,845, incorporated in its entirety herein by reference, and preparations of a levorotatory isomer of modafinil was described in U.S. Pat. No. 4,927,855. Heterocyclic derivatives of modafinil are disclosed in U.S. patent application No. 60/204,789, incorporated in its entirety herein by reference.

Modafinil has been approved for use in humans in 100 mg and 200 mg solid unit dose forms in the U.S. It is also desirable to formulate modafinil in liquid compositions. It has been observed that modafinil has very poor water and lipid solubility and it is therefore difficult to solubilize modafinil in pharmaceutically-acceptable compositions. Conventional solid and liquid formulations that include modafinil are described in the '290 patent. Liquid suspensions or emulsions of modafinil were mentioned in U.S. Pat. No. 5,618,845. A suspension of modafinil was reported in U.S. Pat. No. 5,180,745.

It has been discovered that the solubility of a modafinil compound in pharmaceutically acceptable solvents is difficult and unpredictable. The inventors have discovered that many of the solubilizing agents were either not USP/NF listed, or they had toxicity profiles which did not allow their use at levels higher than a few tenths of a percent. The purpose of this invention is to overcome these problems and formulate a pharmaceutically acceptable composition of a modafinil compound and to provide for effective bioavailable delivery of a modafinil compound to a subject in need thereof.

SUMMARY OF THE INVENTION

Accordingly, one object of the present invention is to provide pharmaceutical compositions comprising a modafinil compound in solution. Particularly, the compositions of the present invention are non-aqueous and optionally comprise other excipients. Preferably, the compositions comprise at least one organic solvent.

It is another object of the invention to provide a method of treating a disease or disorder in a subject which comprises administering to the subject a therapeutically effective amount of the compositions of the present invention.

These and other objects, which will become apparent during the following detailed description, have been achieved by the inventors' discovery that despite its poor solubility, a modafinil compound can be formulated as a pharmaceutical composition, wherein the modafinil compound is bioavailable upon administration to a subject in need thereof.

DETAILED DESCRIPTION OF THE INVENTION

Thus, in a first embodiment, the present invention provides a pharmaceutical composition comprising a modafinil compound in solution. Preferably the pharmaceutical composition is non-aqueous. Preferably the pharmaceutical composition comprises modafinil.

As used herein, a "pharmaceutical composition" refers to a composition that is pharmaceutically acceptable.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "a modafinil compound" or "modafinil compound" and the like, refers to modafinil, its racemic mixtures, individual isomers, acid addition salts, such as a metabolic acid of modafinil, benzhydrylsulfinylacetic acids, and its sulfone forms, hydroxylated forms, polymorphic forms, analogs, derivatives, cogeners and prodrugs thereof. Prodrugs are known in the art as compounds that are converted to the active agent (a modafinil compound) in the body of a subject. These and other modafinil compounds, and their preparation, have been disclosed in U.S. Pat. Nos. 4,177,290, 4,927,855, 5,719,168 and in U.S. patent application No. 60/204,789. In preferred embodiments, the modafinil compound is modafinil.

As used herein, a "solution" refers to a chemically and physically homogeneous mixture of two or more substances. The solution may comprise a solid dispersed in a liquid, solid or semi-solid medium. Preferably the solution comprises a solid in a liquid medium. In more preferred embodiments, the solid that is solubilized is a particle of molecular dimensions. In context of the present application, a solution does not include inclusion complexes, such as those complexations of a drug with cyclodextrins.

As used herein, a "non-aqueous" composition refers to a composition that contains from 0–10% water by weight.

As used herein, a "polyol" refers to an alcohol with more than one hydroxy group. Examples include, but are not limited to glycols, such as ethylene glycol and propylene glycol, and other diols; glycerol, and other triol derivatives; and sugar alcohols.

As used herein, a "lower alkyl alcohol" refers to a branched or straight-chained $C_1$–$C_6$ alkyl group containing one hydroxy group, such as ethanol, n-propanol, isopropanol, n-butanol, isobutyl alcohol, sec-butyl alcohol, t-butyl alcohol, pentanol, hexanol, etc; with preferred lower alkyl alcohols including ethanol, propanol and isopropanol.

As used herein, the term "arylalkyl alcohol" refers to an aryl-substituted $C_1$–$C_6$ alkyl group containing one hydroxy group, such as benzyl alcohol, phenethyl alcohol, diphenyl-methyl alcohol (benzhydrol), etc.; with preferred arylalkyl alcohols including benzyl alcohol, α-phenethyl alcohol and β-phenethyl alcohol.

As used herein, "therapeutically effective amount" refers to an amount which is effective in reducing, eliminating, treating, preventing or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, "bioavailable" refers to a portion of the administered dose that is absorbed in the blood stream and can readily be determined by techniques known in the art, such as, for example, by measuring the blood serum level of a compound.

As used herein, the term "subject" refers to a warm blooded animal such as a mammal, preferably a human or a human child, which is afflicted with, or has the potential to be afflicted with one or more diseases and conditions described herein.

As used herein, "unit dose" means a single dose which is capable of being administered to a patient, and which can be readily handled and packaged, remaining as a physically and chemically stable unit dose, comprising either a modafinil compound or a pharmaceutically acceptable composition comprising a modafinil compound.

As used herein, "excipients" refers to substances that are used in the formulation of pharmaceutical compositions, and, by themselves, generally have little or no therapeutic value. Typical excipients include antioxidants, anti-bacterial agents and other preservatives; chelating agents; buffering agents; agents for adjusting toxicity; coloring, flavoring and diluting agents; emulsifying and suspending agents; and other substances with pharmaceutical applications.

As used herein, the term "about" refers to a range of values ±10% of a specified value. For example, the phrase "about 200" includes ±10% of 200, or from 180 to 220.

In certain preferred embodiments, the compositions comprise a modafinil compound in any pharmaceutically acceptable solvent. The selection of a suitable solvent is one that solubilizes a modafinil compound in an amount of at least 1 mg/ml. It is understood that "adequate solvent", or "adequate solubility" refers to a composition which gives a solubility of at least 1 mg/ml. A "poor solvent" or "poor solubility" refers to a composition which gives a solubility of less than 1 mg/ml.

Preferably, the solubility of modafinil is at least about 1 mg/ml. In certain embodiments, the solubility of a modafinil compound is from about 1 to about 500 mg/ml. In certain more preferred embodiments, a modafinil compound is present from about 1 to about 200 mg/ml. In other more preferred embodiments, the solubility of a modafinil compound is from about 5 to about 100 mg/ml, and in most preferred embodiments, from about 5 to about 80 mg/ml.

In certain embodiments of the invention, the compositions comprise at least one organic solvent. A suitable organic solvent can readily be determined by one skilled in the art, and is one which is pharmaceutically acceptable and imparts adequate solubility of a modafinil compound. In certain preferred embodiments, there are three solvents, and other more preferred embodiments include one or two solvents. In certain preferred embodiments, the amounts of any additional solvents comprise from about 0.5% to about 50% (v/v) of the composition, with a more preferred amount of about 1% to about 50%, and a most preferred amount about 5% to about 20% (v/v).

In certain preferred embodiments, the organic solvent is diethylene glycol monoethyl ether, propylene carbonate, dimethyl isosorbide, 1-methyl-2-pyrrolidinone ("NMP"), medium chain length monoglycerides, or a polyol. A highly purified diethylene glycol monoethyl ether is Transcutol™. Medium chain length monoglycerides include glyceryl monocaprylate (Imwitor®), glyceryl caprylate/caprate (such as Capmul®) and polyoxyethylene glyceryl caproate (such as Labrasol®). Polyols include glycerin, propylene glycol, 1,4-butane diol, 1,3-butane diol, hexylene glycol, tetraglycol (also known as glycofuranol), or polyethyleneglycols. Preferred polyols include polyethylene glycols or "PEG", which refer to a liquid or solid polymer of the general formula $H(OCH_2CH_2)_nOH$, wherein n is at least 4. The preferred PEG has an average molecular weight of from about 200 to about 5000 Daltons, with a more preferred PEG from about 300 to about 2000 Daltons and a most preferred PEG from about 300 to about 1500 Daltons. Commercially available PEG materials include PEG-200, PEG-300, PEG-400, PEG-540, PEG-600, PEG-800, PEG-1000 and PEG-1450. All are commercially available from, for example, from Union Carbide Corporation in both food or pharmaceutical grades. Particularly preferred PEG solvents for use in the present composition include PEG-300, PEG-400 and PEG 1450, with PEG-300 and PEG-400 being more particularly preferred.

In other preferred embodiments, the compositions comprise additional solvents, which can be any organic solvent that adequately solubilizes a modafinil compound. Appropriate additional solvents can be readily determined by one skilled in the art and are ones which are pharmaceutically acceptable and improve the solubility of a modafinil compound. Preferably, the additional solvents comprise an organic solvent. The additional solvents may be selected from the organic solvents enunciated above, with a preferred solvent being a polyol. In certain preferred embodiments, an additional, or second solvent comprises a lower alkyl alcohol or an alkylaryl alcohol, and more preferably an alkylaryl alcohol, such as benzyl alcohol, α-phenethyl alcohol or β-phenethyl alcohol.

In more preferred embodiments, the solvent system includes mixtures of a polyethylene glycol and an arylalkyl alcohol. More preferred embodiments include mixtures of the preferred polyethylene glycols and arylalkyl alcohols, for example PEG-400 and benzyl alcohol, PEG-400 and α-phenethyl alcohol, PEG-400 and β-phenethyl alcohol, and PEG-300 and benzyl alcohol, etc. In other more preferred embodiments, the compositions comprise from about 80% to about 99% PEG-400, and from about 1% to about 20% benzyl alcohol (v/v). A further preferred embodiment, the compositions comprise from about 90% to about 99% PEG-400, and from about 1% to about 10% benzyl alcohol (v/v). In most preferred embodiments, the compositions comprise 95:5 (v/v) PEG-400:benzyl alcohol. In certain preferred embodiments, the compositions comprise a modafinil compound, or preferably, modafinil, at a concentration of about 1 to about 100 mg/ml, preferably from about 1 to about 60 mg/ml and more preferably from about 20 to about 50 mg/ml; a first organic solvent selected from glycerin, propylene glycol, diethylene glycol monoethyl ether, propylene carbonate, a medium chain length monoglyceride, dimethyl isosorbide, and a polyethyleneglycol; and a second organic solvent selected from a lower alkyl alcohol and an arylalkyl alcohol.

In certain further preferred embodiments, the first organic solvent is a polyethyleneglycol, and the second organic solvent is an alkylaryl alcohol. In more preferred embodiments, the first organic solvent is PEG-300 or PEG-400, and the arylalkyl alcohol is benzyl alcohol.

In certain preferred embodiments, the compositions comprise at least one unit dose of a modafinil compound. In certain more preferred embodiments, the compositions comprise one unit dose of a modafinil compound. Preferably, the modafinil compound is modafinil. Daily doses of modafinil preferably range from about 0.01 to 100 mg/kg of body weight. By way of general guidance, daily doses for humans range from about 0.1 mg to about 2000 mg. Preferably the unit dose range is from about 1 to about 500 mg administered one to four times a day, and even more preferably from about 10 mg to about 400 mg, administered one to two times a day. In certain preferred embodiments, the unit dose is 100 or 200 mg. In other preferred embodiments, a unit dose is one that is necessary to achieve a blood serum level of about 0.05 to about 30 $\mu$g/ml, and more preferably, of about 1 to about 20 $\mu$g/ml in a subject.

In a further embodiment of the present invention, there is provided a method of treating a disease or disorder in a subject, comprising administering a therapeutically effective amount of a modafinil compound, or preferably a modafinil compound, in a non-aqueous, pharmaceutical composition to a subject in need thereof. In preferred embodiments, the composition is a solution.

In certain other embodiments, the pharmaceutical compositions are useful for treatment of sleepiness, such as excessive daytime sleepiness associated with narcolepsy, or sleepiness associated with sleep apneas, tiredness, Parkinson's disease, cerebral ischemia, stroke, sleep apneas, eating disorders, attention deficit hyperactivity disorder, cognitive dysfunction or fatigue, such as fatigue resulting from multiple sclerosis ("MS fatigue"); and for promotion of wakefulness, stimulation of appetite, or stimulation of weight gain.

The administration of a therapeutically effective amount of the composition can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

A therapeutically effective amount of a modafinil compound will vary depending upon a number of factors, including the dosage of the drug to be administered, the chemical characteristics (e.g., hydrophobicity) of the compounds employed, the potency of the compounds, the type of disease, the diseased state of the patient, and the route of administration. Generally, treatment is initiated with small dosages, which can then be increased by small increments until the optimum desired effect under the circumstances is achieved.

In a further embodiment, the present invention provides for pharmaceutically acceptable compositions comprising a modafinil compound, wherein upon administration of the compositions to a subject, the modafinil compound has a blood serum level of about 0.05 to about 30 $\mu$g/ml in said subject. In a preferred embodiment, the modafinil compound has a blood serum level of about 1 to about 20 $\mu$g/ml in said subject. In another preferred embodiment, the composition being administered to achieve the desired blood serum levels is a non-aqueous, pharmaceutical composition comprising a modafinil compound. In more preferred embodiments, the modafinil compound is modafinil.

In a further embodiment, the present invention provides for compositions that are suitable for oral administration to a subject. Oral administration includes ingestion in the form of a liquid composition, including a syrup, elixir, or emulsion; or as a capsule.

The subject compositions are contemplated to be suitable for administration in capsule form, such as hard and soft gelatin capsules and starch capsules. The hard and soft gelatin capsules are made from gelatin blends as fully discussed in *The Theory and Practice of Industrial Pharmacy*, 3d Ed., Lachman et al., p. 374–408 (Lea & Febiger, 1986), which is hereby incorporated by reference in its entirety. The gelatin can be blended with plasticizers, such as glycerin USP and sorbitol USP, and water. The gelatin capsules can also contain such additives as preservatives, colorants, flavorants, etc. Commercially available gelatin capsules are these made by CAPSUGEL, a division of Warner-Lambert Co., which are available in a general capsule size range of from #5 to #000 having volumes of from about 0.1 to about 1.4 ml. Furthermore, the capsules of the present compositions may be coated with an enteric coating which inhibits degradation of the capsule in the acidic environment of the stomach. Such enteric coatings are widely known in the art, such as in U.S. Pat. No. 5,206,219, the disclosure of which is incorporated herein by reference.

In certain embodiments, the compositions optionally comprise other excipients. The appropriate excipients can readily be determined by one skilled in the art, and may also include antibacterial agents, such as methyl paraben; antioxidants, such as ascorbic acid, sodium bisulfite, and fatty acid esters of ascorbic acid, such as ascorbyl palmitate; chelating agents, such as ethylene diaminetetraacetic acid; buffers, such as acetates, citrates or phosphates; agents for the adjustment of toxicity, such as sodium chloride or dextrose; flavorings; sweetening agents and coloring agents; diluents and binders; emulsifying and suspending agents; and other excipients which may be deemed useful by one skilled in the art, such as those found in *The Handbook of Pharmaceutical Excipients*, 2nd Ed., (The Pharmaceutical Press, London and American Pharmaceutical Association, 1994), which is hereby incorporated by reference in its entirety.

The compositions of the present invention comprise modafinil compounds, which may be readily prepared by one skilled in the art using conventional methods. Methods for preparing modafinil and various derivatives appear in U.S. Pat. No. 4,177,290, and methods for preparing other modafinil compounds appear in U.S. Pat. Nos. 4,927,855, 5,719,168 and in U.S. patent application No. 60/204,789.

There is wide latitude in formulation of the compositions of the present invention. The compositions of the present invention may be a liquid, semi-solid, or solid at room temperature. For example, higher molecular weight PEGs, such as PEG-600 are solid at room temperature, and would require heating to liquefy the PEG and to dissolve the modafinil compound. These PEG solutions may remain warm, or cooled to room temperature, as is required for the desired mode of administration. For example, an oral formulation is the form of a gelatin capsule may utilize a cooled solution of PEG-600. Whether a composition according to the invention is a liquid, semi-solid, or solid at room temperature, may depend upon the selection of components, or other concerns such as commercial viability, administration and the like.

Compositions whose inert or non-active components (i.e., components other than modafinil) are all liquid at room temperature can be prepared by simply mixing the components without heating. The desired amount of a modafinil compound can be weighed out and dissolved in the mixture of inert components, without heating. Moderate heating, preferably less than 60° C., can be applied to hasten complete mixing of the inert components, to hasten dissolution of a modafinil compound, or both.

Preparation of compositions comprising one or more components that are solid at room temperature is carried out at a moderately elevated temperature, preferably less than 60° C. For example, PEG-1450 at room temperature is a solid and gentle heating from between about 40 to about 60° C. liquefies PEG-1450 for its use as a solvent. A modafinil compound can then be stirred into the heated liquid PEG solution until dissolved. Upon cooling to room temperature, the solution solidifies, and gentle warming to 40–45° C. yields a clear solution of a modafinil compound in PEG-1450. Care must be taken to avoid excessive heating, which can lead to decomposition of one or more components of the formulation.

The materials, methods, and examples presented herein are intended to be illustrative, and not to be construed as limiting the scope or content of the invention. Unless otherwise defined, all technical and scientific terms are intended to have their art-recognized meanings.

EXAMPLES

A. Materials:

All the materials in the following examples are commercially available or can be readily prepared by one skilled in the art by known or readily available literature methods. The solvents were USP/NF grade or better.

B. Methods:

1. HPLC

The following HPLC method may be used to measure the modafinil compound content in the compositions. Filter a solution saturated with a modafinil compound through a 1.2 $\mu$m syringe filter. Dilute 10 $\mu$L-of the clear solution to 1 mL with 990 $\mu$L of dimethylsulfoxide (Fischer Certified ACS grade). Take 10 $\mu$L of the diluted solution for the HPLC analysis, with the following representative column conditions:

Flow rate: 1.2 mL/min.

Column: ODS, 4.6×20 mm, Column Temp: 30° C.

Mobil phase: 80%(65% Acetonitrile/35%1M phosphate buffer)

20% water

Analysis time: 5 minutes

Wavelength: 222 nanometers

Concentration can be calculated by comparison to area from a modafinil compound standard used at 0.4 mg/mL with appropriate dilution.

2. Method for Measurements of Blood Level in Rats Given Modafinil Solutions

Allow adult male Sprague-Dawley rats to fast overnight prior to administration. Administer each formulation to the rats via oral gavage, with the dose of a modafinil compound being 100 mg/kg in a dose volume of 3.3 ml/kg. Collect blood from the lateral tail vein at 0.25, 0.5, 1, 2, 4 and 6 hours post dose. Collected the blood on wet ice and spin at 13,000 RPM for 10 minutes. Collect and freeze the supernatant (plasma) on dry ice, and store at −70° C. until analysis. The blood serum levels of the modafinil compound in these experiments can be measured by LC/MS.

Example 1

Preparation of 95:5 (v/v) PEG-400:Benzyl Alcohol.

A mixture of 95 mL of PEG-400 and 5 ml of benzyl alcohol was stirred at room temperature until homogeneous. To a separate container, 0.1 gram of modafinil was weighed and 1 mL of the mixed solvent was added with stirring and heating to 55–60° C. The solution was allowed to cool to room temperature and any undissolved solid was removed by filtering the solution. In the case of a viscous solution or a solution that solidifies at room temperature, warming until a freely flowing solution was obtained and then filtration gave a solution free of particulate matter.

The solubility of modafinil was 61 mg/ml, as measured by HPLC.

Example 2

Blood Serum Levels of Modafinil in Rats

The blood serum levels of midafinil in rats, upon administration of composition of Example 1 is shown below in Table 1. The Oraplus® composition is intended to mimic the bioavailability of solid modafinil dosed in an oral fashion such as a tablet, but without the difficulty of administering a tablet to the rat Oraplus® is an oral suspending vehicle that is commercialy available (Paddock Laboratories), Minneapolis, Minn. ), and is primarily composed of purified water, microystalline cellulose, sodium carboxymethylcellulose, xantham gum, carrageenan, citric acid and sodium phosphate (as buffers), simethicone (antifoaming agent,) and potassium sorbate and methyl paraben (preservatives).

TABLE 1

Blood Serum Levels of Modafinil in Rats

| Modafinil Solutions | BLOOD SERUM LEVEL (ng/ml) | |
| --- | --- | --- |
| TIME (Hrs.) | Example 1 | Oraplus |
| 0.25 | 2.4 | 3.4 |
| 0.5 | 1.4 | 4.9 |
| 1 | 1.4 | 3.0 |
| 2 | 1.2 | 1.9 |
| 4 | 1.2 | 0.4 |
| 6 | 0.5 | 0.2 |

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A pharmaceutical composition comprising a modafinil compound in solution.

2. The composition of claim 1, wherein the composition is non-aqueous.

3. The composition of claim 1, wherein the modafinil compound is modafinil.

4. The composition of claim 1, optionally with other excipients.

5. The composition of claim 1, wherein the solubility of the modafinil compound is from about 5 to about 100 mg/ml.

6. The composition of claim 5, wherein the solubility of the modafinil compound is from about 10 to about 80 mg/ml.

7. The composition of claim 1, comprising at least one organic solvent.

8. The composition of claim 7, wherein the organic solvent is diethylene glycol monoethyl ether, propylene carbonate, dimethyl isosorbide, a medium chain length monoglyceride, or a polyol.

9. The composition of claim 7, wherein the organic solvent is 1-methyl-2-pyrrolidinone.

10. The composition of claim 8, wherein the polyol is glycerin, propylene glycol, or a polyethyleneglycol.

11. The composition of claim 10, wherein the polyethylene glycol is from about 200 to about 5000 Daltons.

12. The composition of claim 11, wherein the polyethylene glycol is from about 300 to about 2000 Daltons.

13. The composition of claim 12, wherein the polyethylene glycol is from about 300 to about 1500 Daltons.

14. The composition of claim 13, wherein the polyethylene glycol is PEG-300, PEG-400, or PEG-1450.

15. The composition of claim 14, wherein the polyethylene glycol is PEG-400.

16. The composition of claim 7, further comprising an additional solvent selected from a lower alkyl alcohol and an alkylaryl alcohol.

17. The composition of claim 16, wherein the additional solvent is benzyl alcohol.

18. The composition of claim 17, wherein the additional solvent comprises from about 1% to about 50% (v/v) of the composition.

19. The composition of claim 18, comprising a polyethylene glycol and an alkylaryl alcohol.

20. The composition of claim 19, wherein the polyethylene glycol is PEG-400 and the alkylaryl alcohol is benzyl alcohol.

21. The composition of claim 20, wherein the composition is 95:5 (v/v) PEG-400:benzyl alcohol.

22. The composition of claim 1, wherein the modafinil compound is present at a concentration of about 1 to about 100 mg/ml; a first organic solvent is glycerin, propylene glycol, diethylene glycol monoethyl ether, propylene carbonate, a medium chain length monoglyceride, dimethyl isosorbide, and a polyethyleneglycol; and a second organic solvent is a lower alkyl alcohol or an alkylaryl alcohol.

23. The composition of claim 22, wherein the first organic solvent is a polyethyleneglycol, and the second organic solvent is an alkylaryl alcohol.

24. The composition of claim 23, wherein the first solvent is PEG-400 and the second solvent is benzyl alcohol.

25. The composition of claim 24, wherein the composition is 95:5 (v/v) PEG-400:benzyl alcohol.

26. The composition of claim 1, comprising one or more unit doses of a modafinil compound.

27. The composition of claim 26, comprising one unit dose of a modafinil compound.

28. The composition of claim 27, wherein the unit dose is 200 mg.

29. The composition of claim 28, wherein the unit dose is 100 mg.

30. A method of treating a disease or disorder in a subject, comprising administering a therapeutically effective amount of a modafinil compound in solution to a subject in need thereof.

31. A method of treating a disease or disorder in a subject, comprising administering a therapeutically effective amount of a non-aqueous, pharmaceutical composition of a modafinil compound to a subject in need thereof.

32. The method of claim 31, wherein the composition is administered for the treatment of sleepiness, tiredness, Parkinson's disease, cerebral ischemia, stroke, sleep apneas, eating disorders, attention deficit hyperactivity disorder, cognitive dysfunction or fatigue; and for the promotion of wakefulness, stimulation of appetite, or stimulation of weight gain.

33. The composition of claim 30, wherein upon administration of the composition to a subject, the modafinil compound has a blood serum level of about 0.05 to about 30 µg/ml in said subject.

34. The composition of claim 33, wherein the blood serum level of the modafinil compound is from about 1 to about 20 µg/ml.

35. The composition of claim 1, wherein the composition is suitable for oral administration to a subject.

36. The composition of claim 35, wherein the composition is encapsulated within a capsule.

37. The composition of claim 36, wherein the capsule is a soft gelatin capsule.

38. The composition of claim 37, wherein the capsule is a hard capsule.

39. The composition of claim 35, wherein the composition is a syrup or elixir.

* * * * *

UNITED STATES PATENT AND TRADEMARK OFFICE
CERTIFICATE OF CORRECTION

PATENT NO.      : 6,489,363 B2                                         Page 1 of 1
DATED           : December 3, 2002
INVENTOR(S)     : Martin J. Jacobs, Bradley T. McIntyre and Piyush R. Patel It is certified that error appears in the above-identified patent and that said Letters Patent is hereby corrected as shown below:

Column 5,
Line 48, please delete "sleep apneas,".

Column 8,
Line 36, please delete "midafinil" and replace with -- modafinil --.
Line 41, please insert a "period", -- . -- after "rat".

Signed and Sealed this

Twelfth Day of October, 2004

JON W. DUDAS
*Director of the United States Patent and Trademark Office*